United States Patent [19]

Kohri

[11] 4,404,963
[45] Sep. 20, 1983

[54] ENDOSCOPE

[75] Inventor: Kitijiro Kohri, Hachioji, Japan

[73] Assignee: Olympus Optical Co., Ltd., Tokyo, Japan

[21] Appl. No.: 199,866

[22] Filed: Oct. 23, 1980

[30] Foreign Application Priority Data

Oct. 31, 1979 [JP] Japan .................. 54-140647

[51] Int. Cl.³ ............................................. A61B 1/00
[52] U.S. Cl. ........................................................ 128/4
[58] Field of Search ....................................... 128/4-6; 350/96.26

[56] References Cited

U.S. PATENT DOCUMENTS

4,209,228 6/1980 Chikama ........................ 350/96.26
4,216,767 8/1980 Aoshiro ................................ 128/6
4,241,729 12/1980 Aoshiro ................................ 128/4
4,258,721 3/1981 Parent et al. ............................ 128/6

Primary Examiner—Wm. E. Kamm
Assistant Examiner—Max F. Hindenburg

[57] ABSTRACT

An endoscope comprises an internal space extending through the substantially whole length of the endoscope, at least one cylindrical end portion which is connected to the endoscope and provided with an air port open to the outside of the endoscope, only through which the internal space communicates with the open air, and a fluid-proof cap one end of which is open for insertion of the cylindrical end portion and the other end of which is closed, whose inner peripheral wall is shaped complementary to the outer peripheral wall of the cylindrical end portion, and which is provided with an O-ring disposed in the inner peripheral wall to seal in a fluid-tight state between the outer peripheral wall of the cylindrical end portion and the inner peripheral wall of the cap, and also provided with a fitting mechanism for detachably connecting the cap to the cylindrical end portion. Where the cylindrical end portion of the endoscope is pushed into the cap, the cylindrical end portion is sealed in a fluid-tight state. At this time, air held in the internal space of the endoscope is more compressed. When, therefore, fine holes or cracks are produced in the endoscope, the compressed air prevents a washing or disinfecting liquid from being carried into the internal space of the endoscope. Further where the endoscope is dipped in the water, generation of air bubbles in the water informs the operator of the presence of such defective parts as well as the locations thereof.

15 Claims, 11 Drawing Figures

ENDOSCOPE

This invention relates to an endoscope which includes a tubular end portion such as a connector or an ocular section and provided at its end with an opening communicating with a closed space in the endoscope, and a fluid-proof cap which is mounted on the tubular end portion when the endoscope is washed and disinfected.

An endoscope generally comprises an elongate insertion section including an observation optical fiber bundle and an illumination optical fiber bundle. The insertion section is put into the coeliac cavity of a human body (hereinafter simply referred to as "the coeliac cavity") for observation or diagnosis.

A process of examining the coeliac cavity by means of an endoscope has made a rapid progress in recent years. Since endoscopes naturally increase in number, it is demanded to establish a quick, easy, unfailing process of washing and disinfecting an endoscope.

However, an endoscope manufactured to date can not be wholly dipped in a washing or disinfecting liquid due to its specific construction. Therefore, it has been necessary to wash and disinfect the respective sections of the endoscope with a great deal of time and work. Further difficulties have been experienced with respect to the prior art endoscope that when it is repeatedly applied, minute holes or cracks unobservable or unnoticeable to the operator take place in the insertion section, central section or any other part of an endoscope, undesirably resulting in the influx of a washing or disinfecting liquid into the endoscope through such defective parts.

It is accordingly the object of this invention to provide an endoscope in which a cylindrical end portion is fitted with a fluid-proof cap, which, when set in place for practical application, by telescoping over the clindrical end portion, causes compressed air to be introduced into the endoscope, thereby preventing a washing or disinfecting solution from being carried into the endoscope, and enabling the whole endoscope to be washed and disinfected quickly, easily and unfailingly, and further informs the operator of any leakage of the washing or disinfecting liquid from the endoscope and also the location of the leakage.

To attain the above-mentioned object, this invention provides an endoscope which comprises an internal space extending through the endoscope over its substantially whole length, at least one cylindrical end portion which is connected to the endoscope and provided with an air port only through which the internal space of the endoscope communicates with the open air, and a fluid-proof cap which has an inner peripheral wall is complementary to the outer peripheral wall of the cylindrical end portion, and which comprises an O-ring disposed in the inner peripheral wall of the cap to seal between the outer peripheral wall of the cylindrical end portion and the inner peripheral wall of the cap, and fitting means for detachably mounting the cap on the cylindrical end portion, and one end of which is opened to allow for the insertion of said cylindrical end portion, and the other end of which is closed.

Where the cylindrical end portion is forced into the cap, the volume of the internal space of the cylindrical end portion becomes small, causing the air held in the space to be compressed. The compressed air is conducted into the internal space of the endoscope body through the air port of the cylindrical end portion, thereby elevating air pressure prevailing in said internal space. Even if, therefore, fine holes or cracks are produced in the endoscope body, its cylindrical end portion, etc. a washing or disinfecting solution is prevented from flowing into the endoscope through such defective parts. Further, if such fine holes or cracks are formed, compressed air held in the endoscope comes out of the fine holes or cracks in the form of bubbles when the endoscope is dipped in water or a washing or disinfecting liquid, offering the advantage of easily informing the operator of the pressure of such small holes or cracks and effecting the easy repair of such defective parts of the endoscope.

This invention can be fully understood from the following detailed description with reference to the accompanying drawings, in which.

Figure 1:
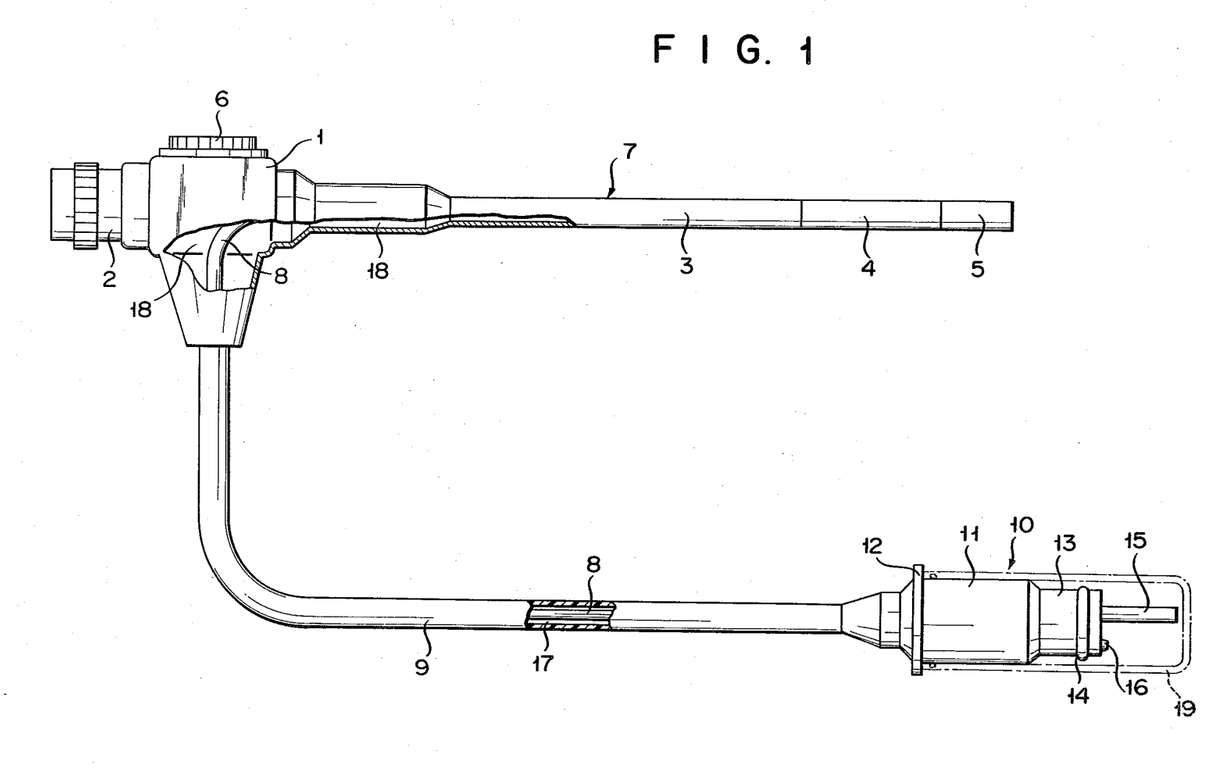
FIG. 1 is a schematic whole front view of an endoscope according to one embodiment of this invention.

Referring to FIG. 1, an endoscope embodying this invention comprises a control housing 1, an ocular section 2 fixed to a proximal end of the control housing 1, an elongate flexible sheath 3 extending from a distal end of the control housing 1, a bend section 4 fixed to the distal end of the sheath 3, and a distal end section 5 fixed to the distal end of the bend section 4.

An operation knob 6 is mounted on one lateral wall of the control housing 1. By means of the operation knob 6, the bend section 4 can be flexed with an optional radius of curvature in any desired direction by means of operation wires (not shown) which extend through the control housing 1, sheath 3 and bend section 4 and whose ends are respectively connected to the operation knob 6 and the proximal end of the distal end section 5. An assembly of the control housing 1, sheath 3, bend section 4 and distal end section 5 is hereinafter referred to as "an endoscope body 7".

An objective (not shown) is set in the distal end section 5. An image guide (not shown) formed of optical fiber bundles extends through the endoscope body 7. The distal end of the image guide is optically connected to the objective, and the proximal end of the image guide is optically connected to an ocular (not shown). A light guide 8 formed of an optical fiber bundle extends through the endoscope body 7 from the distal end of the distal end section 5 (in the case of a front view type endoscope) and from the lateral wall of the distal end section 5 (in the case of a side view type endoscope). The light guide 8 further extends through a flexible umbilical cord 9 from one lateral wall of the control housing 1. A connector 10 which is to be fitted into a receptacle (not shown) of a light source device is fixed to the free end of the umbilical cord 9. The connector 10 comprises a cylindrical body 11 whose rear end is provided with a circular flange 12. A cylindrical insertion section 13 is projectively provided at the forward end of the cylindrical body 11. An annular engagement ridge 14 is formed at the forward end. A light guide tube 15 protrudes from the forward end of the cylindrical insertion section 13. The light guide 8 reaches the free end of the light guide tube 15. The receptacle of the light source device (not shown) has a shape complementary to the outer peripheral wall of the insertion section 13. Where the connector 10 is fitted into the light source receptacle, the cylindrical insertion section 13 is closely fitted into the receptacle. The annular engagement ridge 14 is inserted into an annular groove (not shown) formed in the light source receptacle. As a result, the connector 10 is securely supported in the light source receptacle. Light beams emitted from a light source are conducted to the end of the light guide tube 15.

The above-mentioned endoscope has the same construction as the known type. The endoscope body 7 of this invention are provided with the known endoscope parts. However, description is omitted of the parts which fall outside of the scope and object of this invention.

An endoscope comprises cylindrical end portions, such as the proximal end of the ocular section 2 and the free end (forward end) of the connector 10 which should be protected by being covered in a fluid-proof state when the endoscope is wholly washed or disinfected.

Throughout the embodiments described with reference to FIGS. 2 to 9, the cylindrical end portion requiring the above-mentioned protection is taken to be the connector 10. The free end (forward end) of the connector 10 is provided with an air port 16 through which the internal space 17 of the umbilical cord 9 communicates with the outside of the connector 10. The internal space 17 of the umbilical cord 9 communicates with a closed internal space 18 formed in the endoscope body 7 (FIG. 1).

Figure 2:
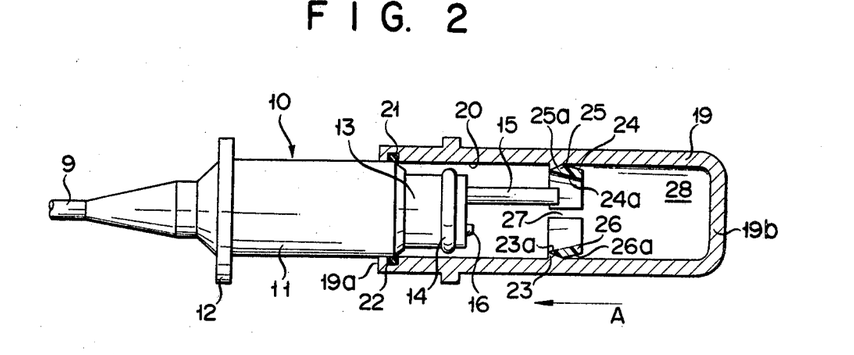
FIG. 2 is a longitudinal sectional view of a fluid-proof cap initially fitted to a light guide connector.
Figure 3:
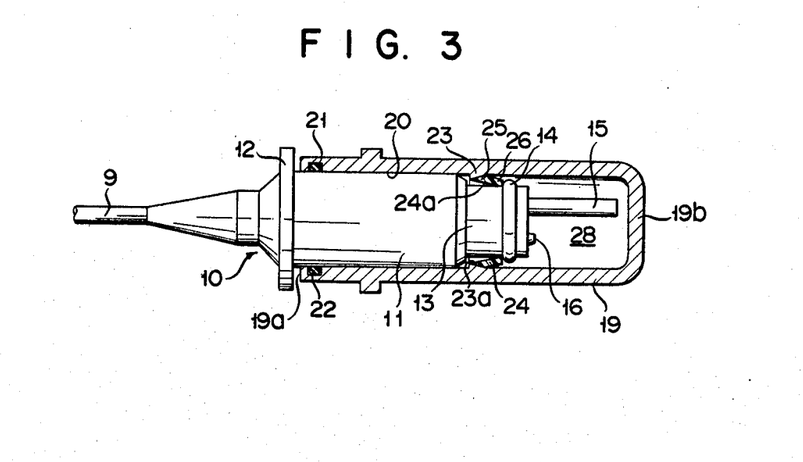
FIG. 3 is a longitudinal sectional view of the fluid-proof cap fully fitted to the light guide connector.
Figure 4:
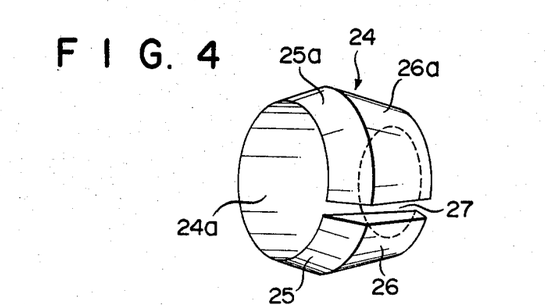
FIG. 4 is an oblique view of an annular fixing member fitted to the fluid-proof cap shown in FIGS. 2 and 3.

Referring to FIGS. 2 to 4 showing an endoscope according to a first embodiment of this invention, a hollow cylindrical fluid-proof cap 19 is prepared from a material such as stainless steel which is not corroded by water and chemicals. One end 19a of the cap 19 is opened, and the other end 19b thereof is closed. The inner peripheral wall 20 of the cap 19 has a diameter substantially equal to the outer diameter of the cylindrical body 11 of the connector 10.

An annular groove 21 is formed in that portion of the inner peripheral wall 20 which lies near said one end 19a. An O-ring 22 prepared from an elastic material such as rubber is fitted into the annular groove 21.

Formed in the intermediate part of the inner peripheral wall 20 of the cap 19 is an annular projection or annular ridge 23 which has a right angled triangular cross section and whose truncated conical inner face 23a is directed toward the closed end 19b of the cap 19.

As best shown in FIG. 4, the cap 19 contains an annular fixing member 24. This fixing member 24 comprises a truncated conical abutting section 25 whose outer peripheral wall 25a is complementary to the inclined plane 23a of the annular projection 23, and a truncated engagement section 26 whose outer peripheral wall 26a projects from the large diameter end of the abutting section 25 and is inclined in the opposite direction to that in which the outer peripheral wall 25a is inclined. The fixing member 24 is set in the cap 19 with the outer peripheral wall 25a pressed against the inclined plane 23a of the annular projection 23.

The inner peripheral wall 24a of the fixing member 24 defines a truncated conical form whose inner diameter progressively decreases as measured from the abutting section 25 toward the engagement section 26. An axially extending notch 27 is formed in the fixing member 24. This fixing member 24 is prepared from an elastic material such as polytetrafluoroethylene. The fixing member 24 is inserted into the cap 19 at its open end 19a. When the fixing member 24 rides over the annular projection 23, the outer diameter of the fixing member 24 is reduced due to the presence of the notch 27. When carried beyond the annular projection 23, the fixing member 24 has its outer diameter returned to the original measurement, and occupies a prescribed position.

Description is now given of the process by which the cap 19 is applied to the cylindrical end portion of the endoscope. As shown in FIG. 2, the cylindrical body 11 of the connector 10 is inserted into the cap 19 until the fixing member 24 is moved beyond the annular projection 23. At this time, the O-ring 22 is pressed against the outer peripheral wall of the cylindrical body 11 to seal between the cap 19 and the cylindrical body 11, thereby rendering the forward end of the connector 10 fluid proof.

Air in the air chamber 28 of the cap 19 is more compressed as the cap 19 is further pushed in the direction of the arrow A. The compressed air passes through the air port 16, the internal space 17 of the umbilical cord 9 and the internal space 18 of the endoscope body 7 to elevate air pressure prevailing in the internal spaces 17, 18 to a higher level than that of the open air. In this case, it is assumed that the internal spaces 17, 18 do not communicate with the open air except through the air port 16.

The above-mentioned arrangement prevents a liquid from being carried into the internal spaces 17, 18 from the outside. When, therefore, the proximal end of the ocular section 2 is enclosed in a cover, the endoscope can be wholly washed and disinfected by water and a chemical solution.

Even where fine holes or cracks are produced in the endoscope body 7 and/or umbilical cord 9, the presence of compressed air in the internal spaces 17, 18 of the endoscope prevents a washing water or disinfecting chemical solution from entering the internal spaces 17, 18 through such defective parts.

Further where fine holes or cracks are present in the endoscope body 7 and/or umbilical cord 9 and the endoscope body 7 is fully dipped in water, a washing liquid or chemical solution, the compressed air held in the internal spaces 17, 18 come out of such defective parts in the form of bubbles into the water or solution. This event infallibly informs the operator of the positions of the defective parts, offering the advantage of ensuring the easy and immediate repair of the endoscope device. Application of the fluid-proof cap 19 further has the merit of enabling the operator to recognize the presence of fine holes or cracks in the endoscope device from the emission of air bubbles through the defective parts, thereby eliminating the necessity of taking any other particular means for inspection of the condition of the endoscope device. Moreover, the fluid-proof cap can be used as a protective cover for the cylindrical end portions of the endoscope device when it is not used for the inspection of the coeliac cavity of the human body.

Figure 5:
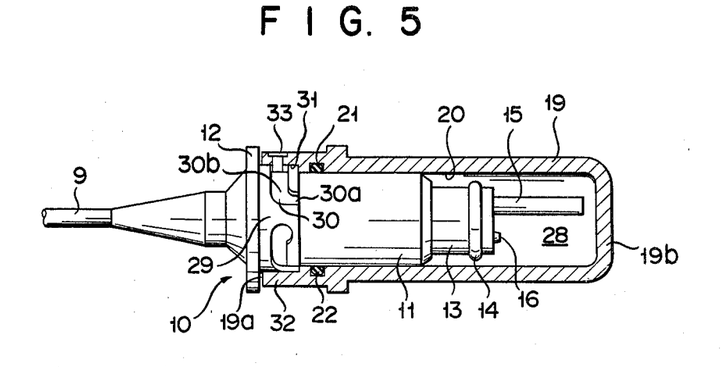
FIG. 5 is a longitudinal sectional view of a fluid-proof cap according to another embodiment of the invention fitted to the light guide connector.

Description is now given of an endoscope of FIG. 5 according to a second embodiment of this invention.

The connector 10 of the second embodiment of FIG. 5 is different from that of the first embodiment of FIG. 1 in the following respects.

That portion of the cylindrical body 11 which lies adjacent to the circular flange 12 constitutes a cylindrical larger diameter section 29. Equidistantly arranged in the larger diameter section 29 in the circumferential direction are L-shaped grooves 30 each consisting of an axial groove portion 30a axially extending from the insertion section 13 of the cylindrical body 11 and circumferential groove portion 30b circumferentially extending and formed contiguously to the axially groove portion 30a.

That portion of the fluid-proof cap 19 which lies adjacent to the open end 19a thereof constitutes an engagement section 32 whose larger diameter inner peripheral wall 31 has the same inner diameter as the outer diameter of the cylindrical larger diameter section 29. Projectively provided on the engagement section 32 are a plurality of engagement pins 33 in the same number as engagement grooves 30. The inner ends of the pins 33 are aligned with the inner peripheral wall 20 of the cap 19, and further face the circumferential groove portions 30b of the engagement grooves 30.

Where the cylindrical body 11 is inserted into the cap 19 and the pins 33 contact the forward end of the engagement section 32, the cap 19 is rotated in a given direction, causing the pins 33 to be fitted into the axial groove portions 30a of the engagement grooves 30. Later where the cap 19 is pushed until it is brought to rest, and is rotated in the same circumferential direction as the circumferential grooves 30b, then the cap 19 is fixed to the connector 10. In other words, the cylindrical larger diameter section 29, engagement grooves 30, engagement section 32 and pins 33 jointly constitute means for fixing the cap 19. When the above-mentioned operation steps are reversed, the cap 19 is removed from the connector 10. The other functions of the second embodiment of FIG. 5 are the same as those of the first embodiment of FIG. 1.

Figure 6:
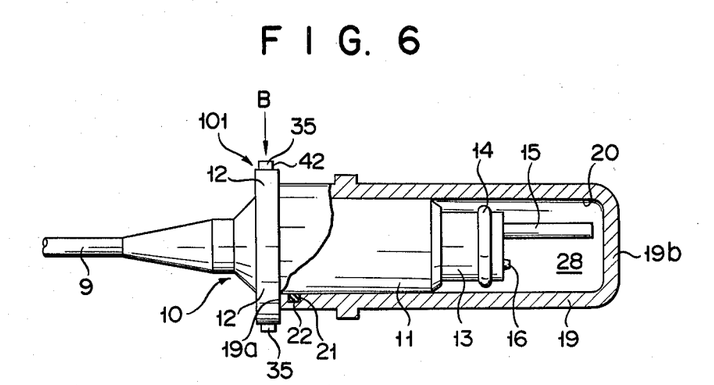
FIG. 6 is a longitudinal sectional view of a fluid-proof cap according to still another embodiment of the invention fitted to the light guide connector.
Figure 7:
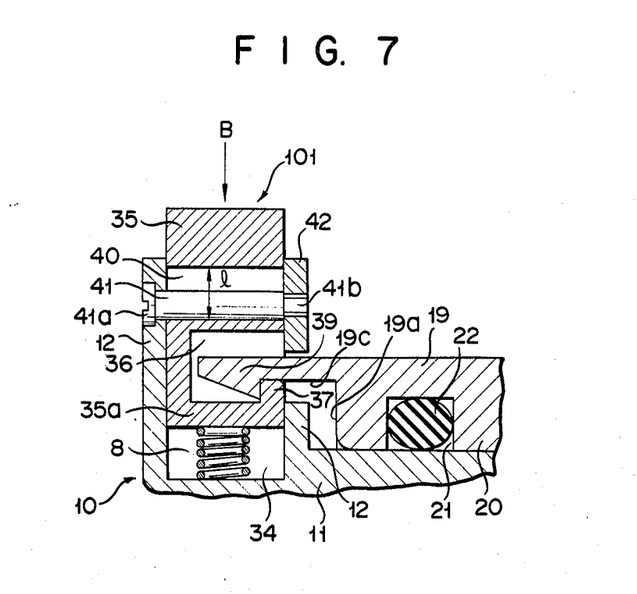
FIG. 7 is a longitudinal sectional view of a mechanism for fixing the fluid-proof cap of FIG. 6.

Description is now given of an endoscope of FIGS. 6 and 7 according to a third embodiment of this invention which comprises different means for fixing the fluid-proof cap 19 from those of the first and second embodiments.

The fluid-proof cap fixing means of the third embodiment has a mechanism 101. A pair of blind holes or engagement block chambers 34 (preferably square holes) are provided which extend inward from the outer periphery of the circular flange 12 of the connector 10 and diametrically face each other. Engaged with the blind holes 34 are engagement blocks 35 whose outer peripheral wall has a complementary shape to that of the blind holes 34.

A parallelepiped hole 36 open to the distal end side of the connector 10 is provided nearer to the axis of the connector 10 as measured from the intermediate part of the engagement block 35. Pawls 37 project from that end of a base portion 35a defining the innermost walls of the horizontal parallelepiped holes 36 which face the distal end of the connector 10 toward the outermost wall of the holes 36, that is, radially toward the outside of the connector 10. The engagement block 35 is always radially urged toward the outside of the connector 10 by a compression coil spring 38 which is provided in the blind hole 34, and the respective ends of which are respectively pressed against the inner wall of the engagement block 35 and the bottom wall of the blind hole 34.

The inner peripheral wall 19c of the open end 19a of the cap 19 has a larger diameter than the inner peripheral wall 20 of the cap 19. Pawls 39 extend axially from the open end 19a of the cap 19 so as to be engageable with the pawls 37 of the engagement block 35.

An elongate slot 40 whose cross section extends radially of the connector 10 is formed in that portion of the engagement block 35 which is positioned nearer to the outer portion of the block 35 as measured from the hole 36. Inserted into the slot 40 is a set pin 41 axially penetrating the flange 12. The head 41a of the pin 41 is engaged with the flange 12. The opposite end of the pin 41 to its head 41a is provided with a screw 41b. A nut 42 is threadedly engaged with the screw 41b to fix the pin 41 to this flange 12.

The radial width 1 of the slot 40 and the position taken by the set pin 41 relative to the slot 40 are so determined as to bring about the conditions, in which, when not depressed, the engagement block 35 is radially moved by the spring 38 toward the outside of the connector 10, causing the pawls 37, 39 to engage each other; and when the engagement block 35 is depressed in the direction of an arrow B, the pawl 37 is fully disengaged from the pawl 39. Where, therefore, the operator depresses the engagement blocks 35 by his fingers in the direction of the arrow B, the cap 19 is rendered ready to be released from the connector 10. When the operator's fingers are taken off the engagement blocks 35, the cap 19 is automatically fixed to the connector 10.

Figure 8:
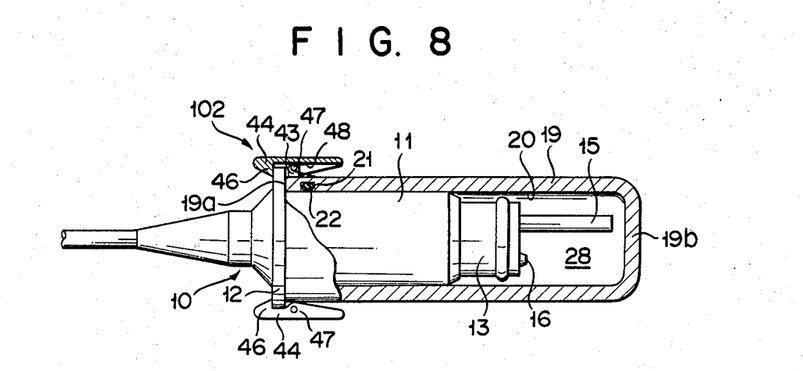
FIG. 8 is a longitudinal sectional view of a fluid-proof cap according to a further embodiment of the invention fitted to the light guide connector.
Figure 9:
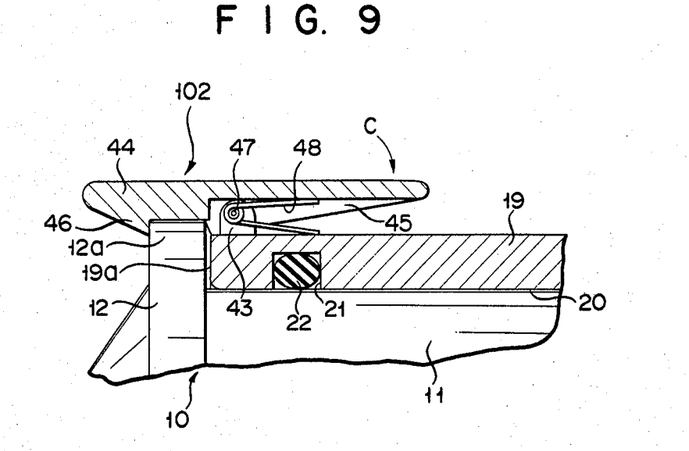
FIG. 9 is a longitudinal sectional view of a mechanism for fixing the fluid-proof cap of FIG. 8.

Description is given of an endoscope of FIGS. 8 and 9 according to a fourth embodiment of this invention. This fourth embodiment comprises the undermentioned mechanism 102 for fixing fluid-proof cap 19.

Radially outwardly extending projections 43 are provided in that outer peripheral portion of the cap 19 which lies near its open end 19a.

Engagement members 44 are each shaped substantially like a triangle as viewed from the lateral side. An axial U-shaped groove 45 is formed in the engagement member 44 in a state extending from the substantially central part to one end of the engagement member 44. The other end of the engagement member 44 is provided with a pawl 46. Each of the engagement members 44 are positioned such that said end of engagement member 44 is directed toward the closed end 19b of the cap 19, whereby the U-shaped projections 43 can be inserted into the corresponding U-shaped grooves 45. The central portion of the engagement member 44 is pivoted to the respective projection 43 by a shaft 47. The shaft 47 is wounded by a tension spring 48. The both arms of the tension spring 48 push the outer wall of the cap 19 and the inner face of the engagement member 44 so that the engagement is elastically urged counter-clockwise in FIG. 9 to allow the pawl 46 to move toward the axis of the cap 19.

In operation, where the connector 10 is fully inserted into the cap 19, the pawls 46 engage the shoulder 12a of the circular flange 12 of the connector 10. As a result, the cap 19 is fixed to the connector 10, and is prevented from readily falling off the connector 10.

Conversely where the opposite ends of the engagement members 44 to the respective pawls 46 are depressed in the direction of an arrow C in FIG. 9 by the operator's fingers against the urging force of the tension springs 48, the pawls 46 are removed from the shoulder 12a of the flange 12 of the connector 10, enabling the cap 19 to be separated from the connector 10.

The foregoing embodiment of FIG. 9 eliminates the necessity of providing the connector 10 with some elements of the fixing member 102, simplifying the construction of the connector 10, and offering the advantage of preventing the original function of the connector 10 from being otherwise obstructed by the attachment of said elements of the fixing member 102.

Figures 10, 11:
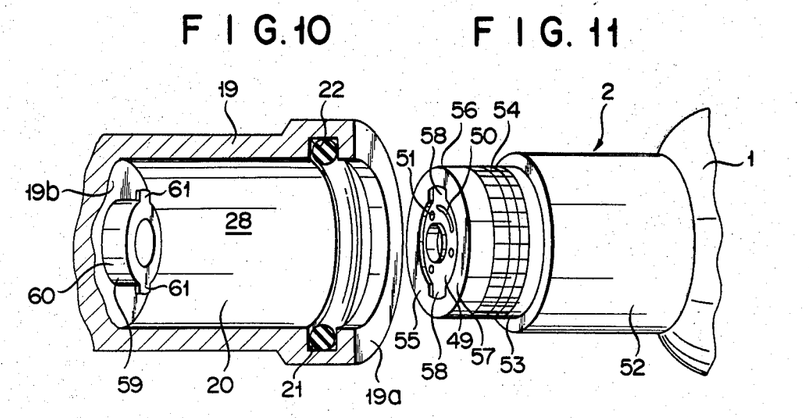
FIG. 10 is a longitudinal sectional view of a fluid-proof cap according to a still further embodiment of the invention.
FIG. 11 is an oblique view of an endoscope ocular section fitted to the fluid-proof cap of FIG. 10.

With reference to FIGS. 10 and 11, description is now given of the case where the cylindrical end portion of the endoscope is the ocular section 2. This ocular section 2 is generally fitted with a photographing camera and other attachments. The end face 49 of the ocular section 2 is provided with openings or air ports (indicated, for example, by reference numerals 50, 51) for communication with the internal space 18 of the endoscope body 7 (FIG. 1). These openings have to be sealed before the endoscope is washed or disinfected.

Referring to FIG. 11, the ocular section 2 comprises a larger diameter cylindrical base portion 52 and a smaller diameter distal end section 53 provided with an ocular diopter-adjusting ring 54. The end face 49 constitutes that of said smaller diameter distal end section 53. Mounted on the end face 49 of the smaller diameter distal end section 53 is an engagement section 55 formed of a ring portion 56 having the same outer diameter as that of the outer peripheral wall of the distal end section 53 and an inwardly extending flange 57. A plurality of notches 58 are formed in the inner edge of the flange 57 in a state diametrically facing each other or equidistantly arranged in the circumferential direction.

Referring to FIG. 10, the fluid-proof cap 19 is a hollow cylindrical member, one end 19a of which is opened, and the other end 19b of which is closed, and is prepared from the same material as that which is used in the other embodiments. The inner peripheral wall 20 of the cap 19 has a diameter substantially the same as the outer diameter of the cylindrical base portion 52 of the ocular section 2. An air chamber 28 is defined by the inner peripheral wall 20 of the cap 19 and the inner wall of the closed end 19b thereof. An annular groove 21 is formed in that portion of the inner peripheral wall 20 of the cap 19 which is disposed adjacent to the open end 19a thereof. An O-ring 22 prepared from an elastic material such as rubber is fitted into the annular groove 21.

An engagement section 59 is provided in the closed end 19b. The engagement section 59 comprises a ring portion 60 having an outer diameter substantially the same as the diameter of the inner edge of the flange 57 of the engagement section 55 of the ocular section 2 and a pair of or a plurality of pawls 61 which are formed on the peripheral wall of that part of the ring portion 60 which is nearer to the open end 19a of the cap 19 for insertion into the notches 58 of the ocular section 2. The pawls 61 diametrically face each other or are equidistantly arranged in the circumferential direction of the ring portion 60.

Where the larger diameter cylindrical base portion 52 of the ocular section 2 is inserted into the cap 19, the O-ring 22 is pressed against the outer peripheral wall of the base portion 52, thereby sealing the ocular section 2. Where the cap 19 is further pushed toward the base portion 52, air in the air chamber 28 of the cap 19 is progressively compressed as in the other embodiments. The compressed air flows into the internal space 18 of the endoscope body 7 (FIG. 1) to compress air held therein, thus ensuring the fluid-proof effect. The presence of fine holes or cracks in the endoscope body can be determined in the same manner as described in connection with the first embodiment.

Where the cap 19 is carried forward until the pawls 61 contact the flange 57 of the engagement section 55 of the ocular section 2, the cap 19 is rotated about its axis by the operator to cause the pawls 61 to be aligned with the notches 58 formed in the inner edge of the flange 57 of the ocular section 2. Where the cap 19 further advances, the pawls 61 are fitted into the notches 58. Where the cap 19 is again rotated, the pawls 61 enter a groove defined between the flange 57 and the end face 49 of the ocular section 2, securely fixing the cap 19 to the connector 10. Where the above-described operation steps are reversed, the cap 19 is disengaged from the connector 10. After all, the cap 19 is coupled to the ocular section 2 in the bayonet form. With the last mentioned embodiment, both engagement sections 55, 59 jointly constitute the fluid-proof cap fixing means.

What is claimed is:

1. In combination:
    an endoscope having at least one end;
    means defining a closed internal air filled space extending through substantially the entire length of the endoscope;
    a cylindrical end portion connected to said one end and having an outer peripheral wall and an air port communicating said internal space to ambient air;
    a hollow cylindrical fluid tight cap member of substantially the same length as said end portion and sized to slide telescopically over said end portion from the outer to the inner end thereof while covering said port;
    means forming a sliding gas tight seal between the inner surface of said cap adjacent the open end thereof and said outer peripheral wall so that movement of said cap from the outer to the inner end of said portion is effective to force air in said cap inwardly through said port to pressurize said closed internal air filled space; and
    latching means for retaining said cap in fully telescoped position on said end member to maintain pressurization of said endoscope.

2. The combination defined by claim 1 in which said endoscope includes an elongated endoscope body, a light guide extending through said endoscope body and further projecting outward therefrom, an umbilical cord which has two ends, and which is penetrated by said light guide, one end being connected to said endoscope body and the other end constituting said one end of the endoscope, and a cylindrical connector which has two ends, one end being fixed to said other end of said umbilical cord and which constitutes said cylindrical end portion.

3. The combination as defined by claim 1 wherein said latching means comprises:

a cylindrical larger diameter section formed on that end of said connector which faces said other end of said umbilical cord and having an outer peripheral wall and an end face remote from said other end of said umbilical cord;

a plurality of L-shaped engagement grooves, each of which includes an axial groove portion open to said end face and a circumferential groove portion connected to said axial groove portion, said grooves being formed in the outer peripheral wall of said cylindrical larger diameter section equidistant from each other;

an engagement section formed in and adjacent to the open end of said cap and whose inner wall has an inner diameter substantially the same as the outer diameter of said larger diameter cylindrical section; and a plurality of engagement pins, projecting radially inwardly from said engagement section, one for each of said grooves.

4. The endoscope according to claim 2, wherein said connector comprises a cylindrical body whose outer peripheral wall is said outer peripheral wall of said cylindrical end portion, a cylindrical insertion section which has an outer peripheral wall and is concentric with said cylindrical body and whose outer diameter is smaller than the outer diameter of the cylindrical body, and an annular engagement ridge formed on said cylindrical insertion section; and said latching means comprises said annular engagement ridge, and an annular member abutted against the inner peripheral wall of the cap, and having a pawl-like longitudinal cross section for engagement with said annular engagement ridge.

5. The endoscope according to claim 2, wherein said latching means is a truncated conical member whose outer and inner peripheral walls have diameters progressively reduced toward the closed end of the cap.

6. The endoscope according to claim 5, wherein said latching means is prepared from an elastic material and is provided with at least one axially extending notch.

7. The endoscope according to claim 6, wherein said latching means comprises said fixing member and an annular projection formed on the inner peripheral wall of the cap for engagement with said fixing member.

8. The endoscope according to claim 7, wherein said annular projection has a truncated conical inner face with a diameter progressively increasing toward the closed end of the cap; and said latching means has an outer peripheral wall shaped complementary to said truncated conical inner face of said annular projection.

9. The endoscope according to claim 2, wherein said latching means comprises:

an outward extending flange formed on said one end of the connector;

a pair of blind radially extending holes which are formed in the flange in diametrically facing relationship;

engagement blocks slidable through said holes;

first pawls axially extending from the open end of the cap;

second pawls which are formed on said engagement blocks and engageable with said first pawls when said engagement blocks are radially moved out of the flange;

and compression coil springs which is provided in the radially extending holes for always radially urging the engagement blocks outward of said flange.

10. The endoscope according to claim 9, wherein each of said engagement blocks is provided with a hole open toward the respective first pawl, and each of said second pawl radially extends through said hole of the engagement block outward of the flange.

11. The endoscope according to claim 10, wherein each of said engagement blocks is provided with a plurality of slots extending radially of the flange in cross section and also extending axially of said engagement block; and the slots are penetrated by axially extending pins fixed to the flange.

12. The endoscope according to claim 1, wherein said latching means comprises:

an outward extending flange formed at said one end of the connector; and engagement members which are pivoted to the peripheral wall of the cap at its open end and are each provided with a pawl engageable with the flange.

13. The endoscope according to claim 12, wherein said latching means further comprises an elastic urging member provided between the outer peripheral wall of the cap and the engagement member to urge the pawl for engagement with the flange.

14. The endoscope according to claim 1, wherein the endoscope comprises an elongate endoscope body having two ends, and an ocular section connected to one of said two ends of said endoscope body and comprising a base portion constituting said cylindrical end portion and inserted in said cap and an end face; and said latching means is a bayonet mechanism provided between said end face of the ocular section and the closed end of the cap.

15. The endoscope according to claim 14, wherein said bayonet mechanism comprises:

an engagement section comprising a first ring portion concentrically formed at the closed end of the cap, pawls radially extending outwardly from said first ring portion and arranged on said first ring in a circumferentially equally spaced relation;

a second ring portion concentrically projecting from said end face of the ocular section;

a flange which radially extends inward from said ring and whose inner edge has a diameter substantially the same as the inner diameter of said first ring portion; and notches which are open to the inner edge of said flange and equidistantly arranged in the circumferential direction of the flange in the same number as the pawls to be engaged therewith.

* * * * *